United States Patent [19]

Herzberg

[11] Patent Number: 4,988,350
[45] Date of Patent: Jan. 29, 1991

[54] DEVICE FOR RECONNECTING A BROKEN BONE

[76] Inventor: Wolfgang Herzberg, Holmer Strasse 165, D2000 Wedel, Fed. Rep. of Germany

[21] Appl. No.: 370,610

[22] Filed: Jun. 23, 1989

[30] Foreign Application Priority Data

Jun. 24, 1988 [DE] Fed. Rep. of Germany ....... 8808123

[51] Int. Cl.⁵ .............................................. A61F 5/04
[52] U.S. Cl. ......................................... 606/65; 606/71
[58] Field of Search ...................... 606/65, 66, 69, 71, 606/67, 70, 89, 53

[56] References Cited

U.S. PATENT DOCUMENTS

| | | | |
|---|---|---|---|
| 2,496,126 | 1/1950 | Haboush | 606/67 |
| 2,699,774 | 1/1955 | Livingston | 606/65 |
| 2,772,676 | 12/1956 | Pohl | 606/65 |
| 2,801,631 | 8/1957 | Charnley | 606/65 |
| 3,489,143 | 1/1970 | Halloran | 606/67 |
| 3,842,825 | 10/1974 | Wagner | 606/66 |
| 4,438,762 | 3/1984 | Kyle | 606/65 |
| 4,621,629 | 11/1986 | Koeneman | 606/65 |
| 4,628,923 | 12/1986 | Medoff | 606/65 |
| 4,791,918 | 12/1988 | Von Hasselbach | 606/65 |

FOREIGN PATENT DOCUMENTS

7228389 5/1973 France .
3006518 of 1981 France .

*Primary Examiner*—Robert A. Hafer
*Assistant Examiner*—Michael Brown
*Attorney, Agent, or Firm*—Toren, McGeady & Associates

[57] ABSTRACT

The device for connecting a fractured bone in the femoral neck is of two-piece construction that includes a bone fastening cover plate (11) and a trochanter supporting plate (20), in which the bone fastening cover plate (11) is provided with a bone screw reception sleeve (13) assuming an angle which, below the trochanter supporting surface, is passed through a cover plate-like section connected with the trochanter supporting plate (20) which bears upon the bone fastening cover plate (11) which, as well as the cover plate-like section are provided with a number of fastening screw perforations (12) which can be brought into coincidence, in which the trochanter supporting surface is so configured as to correspond to the shape of the trochanter so that, on account of the two-piece construction, an improved adaptability to anatomical conditions by an arbitrary combination of the individual components is possible.

8 Claims, 6 Drawing Sheets

DEVICE FOR RECONNECTING A BROKEN BONE

BACKGROUND OF THE INVENTION

The present invention relates to a device for connecting a fractured bone, more particularly within the femoral neck area, consisting of a bone fastening cover plate with fastening perforations that can be connected with the bone by means of a bolt connection and which extends parallel to the longitudinal axis of the bone, a sleeve positioned at an angle to the fastening cover plate for accommodating a bone screw or a bone pin and a trochanter supporting plate.

For the osteosynthesis of pertrochanteric fractures, i.e. for the stable retention of bone fragments in transverse or short oblique fractures it is known to take care of the fractures of the femoral neck by means of dynamic cover plate screws. Such cover plate screws consist of a bone screw which, from the trochanter, i.e. from the greater trochanter which is located laterally on the proximal femoral shaft, is driven or screwed into the proximal fragment and of a bone plate which is fixed to the distal fragment by means of screws. So-called Pohl's plate screws are employed here which consist of the bone plate and a sleeve formed onto the same at an angle for receiving the bone screw or a bone pin, while the bone plate is, by means of a bolt connection, attached to the same extending parallelly to the longitudinal axis of the bone and fitting snugly against the bone.

It is known furthermore to form onto the bone contact plate of such cover plate screws a trochanter supporting plate which projects cranially, thus in the direction of the head, over the actual fastening cover plate or bone contact plate and which has a configuration approximately adapted to the shape of the trochanter and which, subsequent to the cover plate screw being fastened to the bone, fits snugly against the trochanter and thus supports the trochanter. For it has been shown that when the femoral fracture extends into the trochanter or extends as far as underneath the trochanter, the otherwise so ideal technique developed for taking care of a fracture has reached the limits of its efficiency. That is why, in order to improve the efficiency of the cover plate screw in the case of such types of fractures, the known cover plate screws are provided with a trochanter supporting plate. However, it is essential that a cover plate screw provided with a trochanter supporting plate forms a one-piece implant, which presupposes that the surgeon has to have an extensive assortment at his disposal besides the already existing assortment of implants.

According to the DE-A-20 30 249, a device is known intended for surgical purposes for connecting a fractured bone, particularly within the area of the femoral neck which, with the aid of screws that engage into the latter, is connected with a splint, on which, at one of its extremities, a connecting member is disposed that is adjustable at an angle to the bone, which member is mounted on a mounting means constructed so as to have the form of a circular arc, which is rotatably and fixably arranged in a circular cap in the splint, whereby the possibility is provided of making use of differently constructed splints, each splint in this case being equipped solely on one of its ends with a circular cap in which the mounting means can be rotated. Due to the circumstance that the mounting means of the connecting member is secured to the splint, in many instances merely the additional mounting means and no specially constructed splint is required, which is always of advantage when, besides a femoral fracture, a fracture of the femoral neck supervenes which then calls for the employment of a connecting member, whereas, when it is a question of a fracture of the femur, only one splint is required, different forms of splints being made use of here depending on the size of the thigh and the type of the fracture in question. However, owing to the fact that the mounting means is rotatably attached to the splint and that the connection is effected by means of a bolt connection, the possibility cannot be excluded that the mounting means with the connecting member is twisted relative to the splint or that, already when applying and securing the entire device, a displacement of the mounting means relative to the splint takes place, as a consequence of which, in the case of a femoral neck fracture, the femoral neck is displaced within the area of the fracture surface relative to the femur. To this is further added the circumstance that no trochanter supporting surface exists at all. For the mounting means provided and secured to the splint, when the connection is mounted, does not rest against the trochanter, but projects from the trochanter surface while forming an interspace; nor is any provision made for shaping the mounting means so that the trochanter is embraced by section.

The EP-A-0 046 773 relates to a device for fixing the femoral neck and the greater trochanter on the shaft of the femur of a human being. This device is characterized by an angle plate whose leg, constructed as blade portion, is driven axially into the neck and whose other leg constructed as shaft section is fixed on the shaft, as well as by a forked plate that is fastened to the shaft section of the angle plate and/or to the shaft and which fixes the trochanter on the neck. For the purpose of rotating the femoral neck about 90° in order to remove the destroyed point on the femoral neck from the load area and so as to bring a non-destroyed point of the condyle into the load area, the blade portion of the device must be driven into the neck. If the femoral head has a plurality of fractured areas and if, for example, a substantial area of the greater trochanter is worn, in that case the driving in of the blade portion would lead to a further damaging of the femoral head. To this is added the circumstance that in numerous cases a driving in of parts into the femoral neck or into the femoral head is not possible at all, so that this device cannot be employed in all cases of femoral neck fractures This device is constructed in two pieces and consists of a forked plate and an angle plate, the forked plate in this case being displaceable on the shaft section of the angle plate in the longitudinal direction of the shaft; the shaft section of the angle plate and the forked plate have to be fastened to the shaft so as to lie on top of each other by means of screws. This device is constructed exclusively for a fixation of the femoral neck and of the greater trochanter on the shaft of a femur. One proceeds here from the assumption that the fixation becomes necessary for the healing process of a fracture which is e.g. of such a type of double fracture in which the greater trochanter has detached itself from the femoral neck and the femoral neck from the shaft, but also in other cases as, for instance, where the condyle is destroyed within its load area. In that case the femoral neck is separated from the shaft and from the greater trochanter and turned about 90° in such a way that a healthy area of the condylus becomes the load area. It is for this reason that this fixation device has to be provided with a part, viz. the blade portion, which is driven into the neck in order to be able to twist the femoral neck after its separation from the greater trochanter.

A femoral neck implant with a femoral neck plate which, for its attachment to the outside of the femur is, along its longitudinal axis, provided with several reception apertures for cortical screws and which, on its upper area, is provided with a shaft to be implanted extending in an obtuse-angled manner in its longitudinal axis and reaching subtrochanterically as far as into the femoral neck and, possibly, into the femoral head, is known further from the DE-A-35 34 747. In this integrally constructed femora neck implant, its upper area forms a one-piece connected extension approximately adapted or adaptable to the outer contour of the greater trochanter which possesses one or several reception apertures for spongiosa screws to be fastened extending pertrochanterically as far as into the femoral neck or into the femoral head, while the shaft is constructed so as to be externally smooth and a and circularly cylindrical in shape and is, by means of an external thread at its end, detachably fastened in an internal thread recess within the upper area of the femoral neck plate.

It should be possible to use a femoral neck implant constructed in this way with a minor operative effort while maintaining the physiological femoral neck angle, and it should also permit subjecting it to a primary post-operative load in the case of unstable pertrochanieric fractures without the existence of a mechanical breakdown of the effected osteosynthesis. However, what is essentially involved in the case of this femoral neck implant is the fastening of a one-piece femoral neck plate with a formed-on plate-shaped section as trochanter supporting surface. Due to the one-piece construction of the femoral neck plate, no possibility of adaptation to the most widely varied anatomical conditions and no combinability with another implant assortment for pertrochanteric and subtrochanteric femoral fractures is possible.

The DE-A-10 46 827 describes a one-piece connecting device for juxta-artucular bone fractures, in which case said connecting device consists of a shaped member constructed in one piece which is provided with one section as bone fastening cover plate and one section as trochanter supporting surface. Within the area of the trochanter supporting plate, which is constructed so as to extend in the form of a circular arc, drilled holes or perforations for fitting screw pins, fastening screws and the like are provided, while the shaped member of the connecting device is provided with a screw or pin guide sleeve which has an internal thread into which an external thread engages that is constructed within the area of the screw head of the screw pin.

The hip pin according to the DE-A-18 13 807 consists of a shaft plate which is made to fit snugly along the lateral surface of the femoral shaft below the trochanter and which is equipped with a trochanter contact plate and which, furthermore, has a pin portion which is provided with a passage or axial bore that serves to accommodate a compression means which is characterized by an elongated shaft or stem which, on its outermost end, bears swivelable gripping members so that, when the hip pin is tightened, the femoral neck portion to be aligned in its fracture point is urged against the shaft plate fastened to the femur. This connecting device, too, is of one-piece construction.

The U.S. No. 2,443,363 describes a shaft plate for fastening on a femur, in which case the shaft plate consists of an approximately U-shaped sectional member and can, with the aid of an extensible or telescopic section, be varied in its length. Even if this shaft plate is constructed in two pieces, the two-piece construction solely serves the purpose of rendering a variation in length of the shaft plate possible. However, the shaft plate according to this U.S. publication does in no way consist of a bone fastening cover plate with a bone screw reception sleeve and the actual trochanter supporting plate with a perforation for passing through the bone screw reception sleeve of the bone fastening cover plate.

The present invention is based upon the technical problem of providing a device for connecting a fractured bone, more particularly within the area of the femoral neck and to thus provide a cover plate screw for the osteosynthesis of pertrochanteric fractures according to the type described in the beginning which, for the sake of achieving a greater degree of adaptability to anatomical conditions, renders possible an arbitrary combinability wit: a smaller assortment with the existing implant assortment of a manufacturer for pertrochanteric and subtrochanteric femoral fractures.

SUMMARY OF THE INVENTION

This technical problem is solved by the features characterized in claim 1.

On the basis of such a construction, the device according to the invention consists of two parts, viz. the bone fastening cover plate with the sleeve positioned at an angle to the bone fastening cover plate for receiving the bone screw or a bone pin and a cover plate-like section which corresponds roughly to the sectional member with a bone fastening cover plate of the device, or to the cover plate screw with an extending plate-shaped section as trochanter supporting surface which constitutes the actual trochanter supporting surface, in which the sectional member, within the area of its cover plate-shaped section, is constructed in such a way that this cover plate-shaped section, when the device is applied, overlaps the bone fastening cover plate, i.e. the bone fastening cover plate is inserted into the cover plate-shaped section of the sectional member so that the plate-shaped section projects in the cranial direction as trochanter supporting surface over the bone fastening cover plate and is thus capable of supporting the trochanter, while this plate-shaped section of the sectional member corresponds approximately to the shape of the trochanter. For a secure support of the bone fastening cover plate on the sectional member with its trochanter supporting plate, the cover plate-like-constructed section of the sectional member possesses an approximately U-shaped cross-section, while the web which interconnects the two sectional legs preferably has an outward bulge in the form of a circular arc facing the sectional member legs, so that the surface of the sectional member resting against the bone is roughly adapted to the shape of the bone.

It is possible on account of the two-piece construction, on the basis of a modular system, to supplement the existing implant system of the manufacturers as available to the surgeons. By an optional combine ability it is possible to achieve a greater degree of adaptability to anatomical conditions while keeping a smaller assortment in stock.

In addition, the two-piece construction of the device produces economic advantages, for the implant assortment can be restricted to only a few pieces since the possibility exists of combining with each other cover plate screws or devices having different dimensions with the trochanter supporting plate, consisting of the sectional member with the cover plate-like section and the extended, plate-shaped head section. The efficiency of a thusly constructed device with separately constructed trochanter supporting plate is substantially improved even in the case of complicated fracture configurations. To this is added the circumstance that the device possesses a high degree of efficiency, for also complicated forms of fractures can be dealt with.

Advantageous embodiments of the invention are characterized in the subclaims, the embodiment according to which the trochanter supporting plate is provided with means that render the fixation of cerclage wires possible is particularly advantageous. With such a cerclage, the greater trochanter can be tied in a basket-like fashion to the spoon-shaped section of the supporting plate. Since the spoon-shaped section of the supporting plate possesses dimensions and a configuration which are in conformity with the anatomy, the same serves additionally both as a support as well as a shaping means which restores the healing up into a shape which is true to the anatomy. The device is used along with a cerclage when, within the area of the greater trochanter, the comminution is such that the osseous substance no longer is in a condition which admits screwing operations.

BRIEF DESCRIPTION OF THE DRAWINGS

Embodiments of the invention are explained in greater detail below with the aid of the drawings. Thus

DETAILED DESCRIPTION OF THE PREFERRED EMBODIMENT

Figure 1:
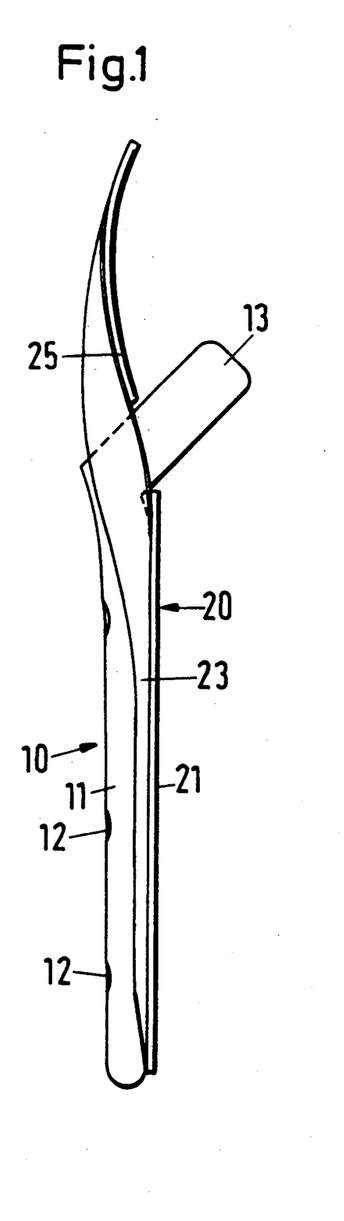
FIG. 1 shows the trochanter supporting plate in combination with the bone fastening cover plate in a side view.
Figure 16:
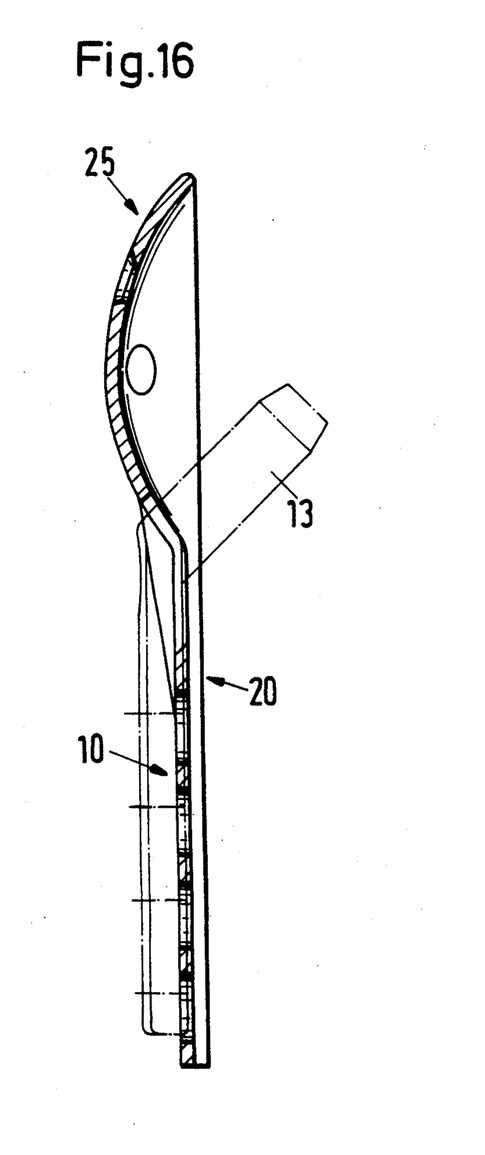
FIG. 16 shows, partly in a side view and partly in a vertical section, the trochanter supporting plate according to FIG. 12 in combination with the bone fastening cover plate.

According to FIG. 1, a device constructed in a manner known per se for connecting a fractured bone, more particularly within the area of the femoral neck, or a cover plate screw 10 is combined with a trochanter supporting plate 20. The device 10 consists of a bone fastening cover plate 11 with a number of perforations 12 constructed in the latter for passing through fastening screws when the device 10 with its bone fastening cover plate 11 is to be secured to a bone. At one end, the bone fastening cover plate 11 carries a sleeve, a cylindrical tube 13 or the like which serves to receive and guide a bone pin or a bone screw not depicted in the drawing, while the sleeve 13 assumes an angle relative to the bone fastening cover plate 11, as is depicted in FIGS. 1 and 16. This device 10 with its bone fastening cover plate 11 and the sleeve 13 is, according to FIGS. 1 and 16, combined with the trochanter supporting plate 20 which constitutes a component of its own in the form of a quite specially constructed shaped member.

Figure 3:
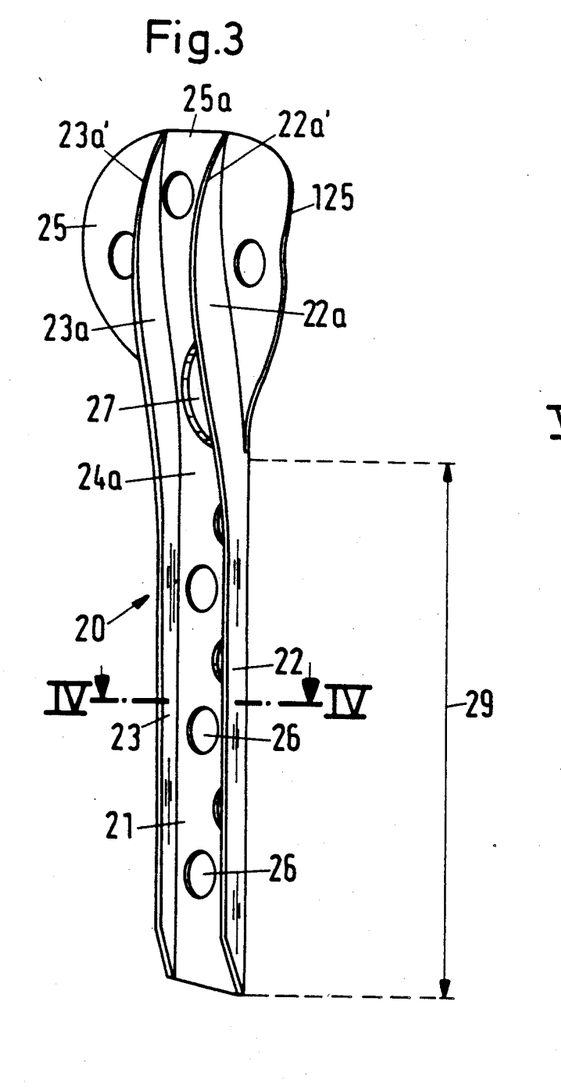
FIG. 3 shows the trochanter supporting plate in a diagrammatical view.
Figure 4:
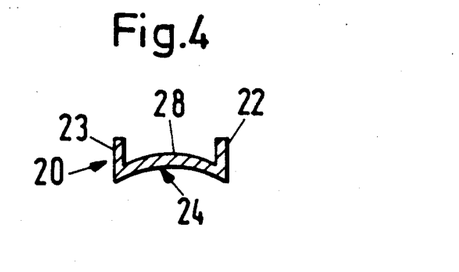
FIG. 4 shows a horizontal section along Line IV—IV in FIG. 3.

This trochanter supporting cover plate 20 consists of a sectional member 21 with a straight or U-shaped cross-section (FIGS. 3 and 4). The two legs forming the sectional member 21 are identified with 22,23, and the web which interconnects the two legs 22,23, is identified with 24. Said sectional member 21 possesses a cover plate-like section 29 which is formed by the legs 22,23 and the web 24. This cover plate-like section 29 of the sectional member 21 corresponds approximately to the shape and construction of the bone fastening cover plate 11 of the device 10.

Figure 2:
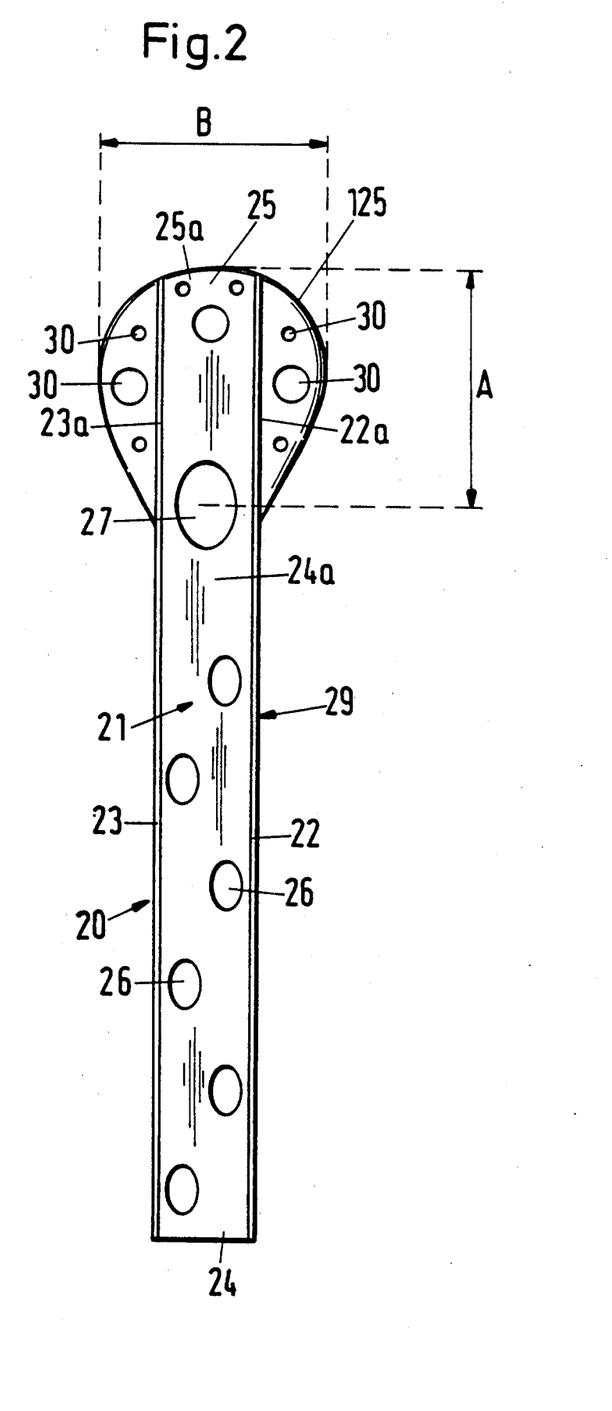
FIG. 2 shows the trochanter supporting plate in a view from below.

On the end 24a of the sectional member web 24 or of the cover plate-like section 29, a plate-shaped section 25 is formed onto the web 24 which extends in a head-like manner or is constructed in a spoon-like manner and forms the supporting surface for the trochanter. Said plate-shaped section 25 with its supporting surface for the trochanter constitutes the actual trochanter supporting plate. This plate-shaped section 25 which forms the supporting surface for the trochanter is provided with a plurality of perforations 30 which serve for the accommodation or the passing through of fastening nails or screws (FIG. 2). In the embodiments depicted in FIGS. 8 and 12, the trochanter supporting plate 20 is provided with three perforations 30',30", of which the two perforations 30' are in side-by-side arrangement and, by preference, are oval in shape, while the third perforation 30" is provided within the upper area of the trochanter supporting plate 20 and is of circular construction.

The web 24 or the cover plate-like section 29 of the sectional member 21 of the trochanter supporting plate 20 has, in its cross-section, a circular arc-like outward bulge 28 which is adapted approximately to the shape of the bone and which faces the two sectional member legs 22,23 (FIG. 4). The shape and the dimensions of this outward bulge 28 correspond approximately to one section of the outward bulge of the bone so that, if possible, a contact over the entire surface of the sectional member 21 with its cove plate-like section 29 against a bone is ensured.

Furthermore, the sectional member 21 is, in its web 24 and in particular in its cover plate-like section 29, provided with a number of fastening perforations 26 which, when inserting the bone fastening plate 11 of the device 10 into the sectional member 21 of the trochanter supporting plate 20, can be made to coincide with the fastening perforations 12 in the bone fastening cover plate 11 of the device 10, so that a simultaneous fastening of the device 10 by means of its bone fastening cover plate 11 and of the trochanter supporting plate 20 is possible. The fastening perforations 26 in the web 24 or the cover plate-like section 20 of the sectional member 21 of the trochanter supporting plate extend into the area of the plate-shaped section 25 which forms the supporting surface for the trochanter (FIGS. 2 and 3).

In addition, the legs 22,23 of the sectional member 21 extend, as is shown in FIG. 3, into the terminal area, indicated at 25a of the plate-shaped section 25 forming the supporting surface of the trochanter, the extended sections of the two legs 22,23 of the sectional member 21 within the area of the plate-shaped section 25 are indicated at 22a,23a. These extended sections 22a,23a of the legs 22,23 of the sectional member 21 of the trochanter supporting plate 20 taper conically toward their extremities 22a',23a'. Moreover, the extended sections 22a,23a of the two legs 22,23 are, within the area of the plate-shaped section 25, adapted to its shape (FIG. 3).

Besides the fastening perforations 26, the web 24 or the cover plate-like section 29 of the sectional member 21 of the trochanter supporting plate 20 possess, within the transitional area to the plate-shaped section 25, an ovaloid recess or perforation 27 which serves for the passing through of the sleeve 13 formed onto the bone fastening cover plate 11 of the device 10 and which is dimensioned in such a way that it is also possible to make use of devices 10 in connection with the trochanter supporting plate 20 in which different angular positions between the sleeve 13 and the bone fastening sleeve 11 exist. Through this ovaloid recess or perforation 27, the bearing screw of the device 10 is passed when the device 10 is inserted into the trochanter supporting plate 20. That is why the ovaloid recess or perforation 27 is dimensioned in such a way that it is possible to use cover plates of all angular values relative to their sleeve 13.

The dimensions of the plate-shaped section 25 of the trochanter supporting plate 20 supporting the trochanter can be selected in an arbitrary manner. According to this the possibility exists of keeping a number of trochanter supporting plates 20 in stock in which the plate section supporting the trochanter or the plate-shaped section 25 may have different sizes, thus different dimensions so that a maximum adaptability to anatomical conditions is ensured at all times when, from a plurality of trochanter supporting plates 20 kept in stock, that particular trochanter supporting plate comes to be used whose plate-shaped section 25 forming the supporting surface for the trochanter corresponds, in its dimensions, to the dimensions of the respective trochanter, upon which the trochanter supporting plate 20 in combination with the device 10 is intended to be brought to bear. The advantage in comparison with the known devices provided with a rigidly forced-on trochanter supporting plate consists here in that the devices 10, whose manufacture is connected with high costs, do not have to be available in a very comprehensive assortment, but that the surgeon is able to manage with a small number of devices 10 if, instead, a larger number of trochanter supporting plates 20 possessing different shapes and adaptations of the plate-shaped section 25 forming the trochanter supporting surface are at his disposal in order to then combine precisely this trochanter supporting plate 20 with the corresponding device 10.

The trochanter supporting plate 20 consists of high-quality material which corresponds to the material from which the known devices are fabricated. These are body-compatible materials, it being also possible for suitable plastic materials to be used if they meet the respective requirements stipulated for such a trochanter supporting plate 20.

The dimensions of the sectional member 21 of the trochanter supporting plate 20 within the area of its cover plate-like section 29 are such that the bone fastening cover plate 11 of the device 10 lying between the two sectional legs 22,23 can be brought to rest on the sectional leg web 24.

Figure 5:
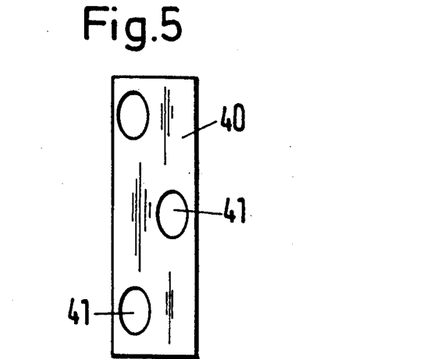
FIG. 5 shows a plate-shaped extension member of short length for the trochanter supporting plate in a top view.
Figure 6:
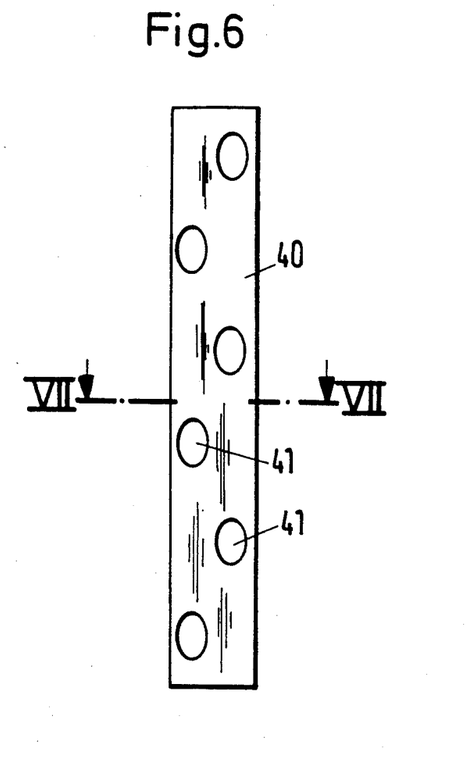
FIG. 6 shows a plate-shaped extension member of greater length for the trochanter supporting plate in a top view.
Figure 7:
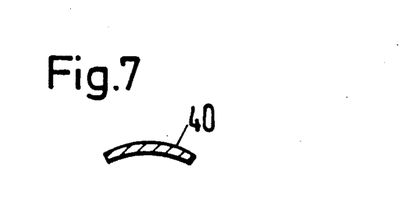
FIG. 7 shows a horizontal section along Line VII—VII in FIG. 6.

In order to be able to extend the cover plate-like section 29 or the web 24 of the sectional, member 21 of the trochanter supporting plate 20, according to FIGS. 5 and 6, plate-shaped extension members having different lengths can be employed. FIG. 5 shows such an extension member 50 having a short length, whereas the extension member according to FIG. 6 possesses a greater length Each extension member 40 is constructed in a plate-shaped and strip-shaped manner and with a width that corresponds roughly to that of the web 24 of the sectional member 21 of the trochanter supporting plate 20. In addition, the extension member is provided with fastening perforations 41. In order to extend the cover plate-like section 29 of the trochanter supporting plate 20, such an extension member 40 is placed upon the web 24 and inserted between the two sectional member legs 22,23 in such a way that the fastening perforations 41 of the extension member 40 come to lie in full coincidence with the fastening perforations 26 in the cover plate-like section 29 or of the web 24 of the sectional member of the trochanter supporting plate 20. Over and above this there also exists the possibility of constructing, within the area of the sectional member legs 22,23 or on the web 24, guideways not depicted in the drawing, in order to be able to insert and retain such a plate-shaped extension member 40. Thus, inter alia, the possibility exists of disposing, in the oppositely located wall areas of the two sectional member legs 22,23, adjacent to the web 24 or the cover plate-like section 29, guide grooves which then serve to accommodate an extension member 40, which is then merely inserted into said guide grooves. As is shown by FIG. 7, also the plate-shaped extension member 40 is provided with a circular arc-shaped section corresponding to the outward bulge section of the web 24 of the sectional member 21 of the trochanter supporting plate. The extension member 40 consists of the same material from which the device 10 and the trochanter supporting plate 20 are fabricated.

The areas identified with A' and B' indicate the variability of the dimensions of the trochanter supporting surface.

Figure 12:
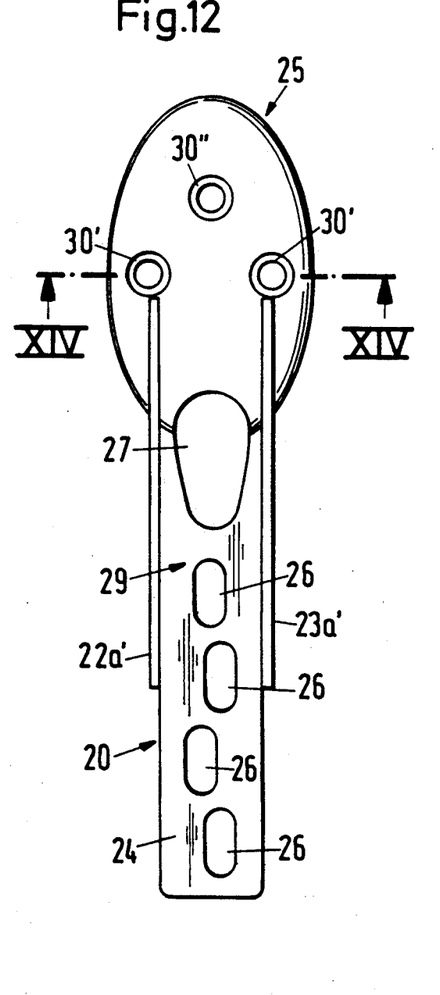
FIG. 12 shows a trochanter supporting plate with stabilizers in a view from below.
Figure 13:
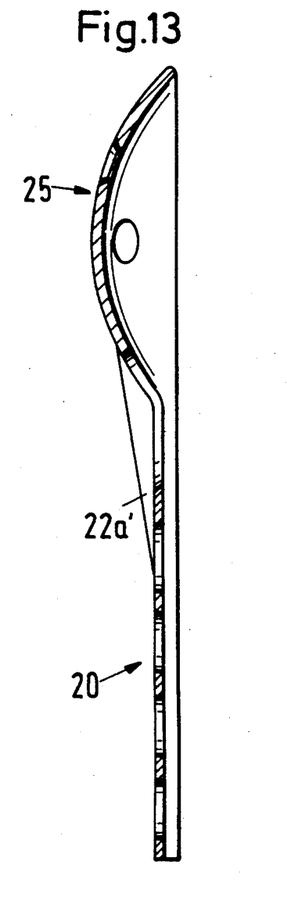
FIG. 13 shows a side view of the trochanter supporting plate according to FIG. 12 in a side view.
Figure 15:
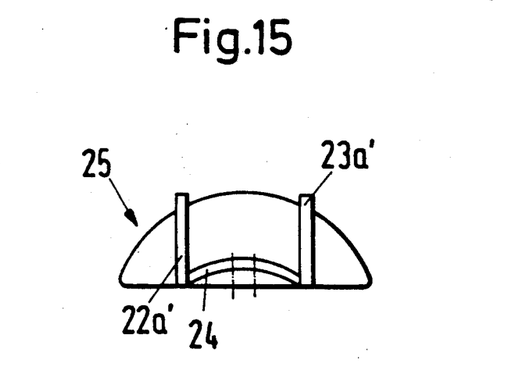
FIG. 15 shows the trochanter supporting plate in a front view.

In the embodiment illustrated in the FIGS. 8 to 11, the supporting surface of the trochanter supporting plate 20 is constructed in a spoon-like fashion and, on its rearward area is provided with reinforcing webs 22a', 23a' merging into the cover plate-like web 29, which correspond to the extended sections 22a,23a of the embodiment according to FIGS. 2 and which extend on both sides of the longitudinal edges 29',29" of the cover plate-like web 29 (FIGS. 12,13,15). These two reinforcing webs 22a,23a pass into the rounded portion of the spoon-shaped supporting surface of the trochanter supporting plate 20 and extend approximately to the two perforations 30' in the spoon-shaped supporting surface.

Figure 8:
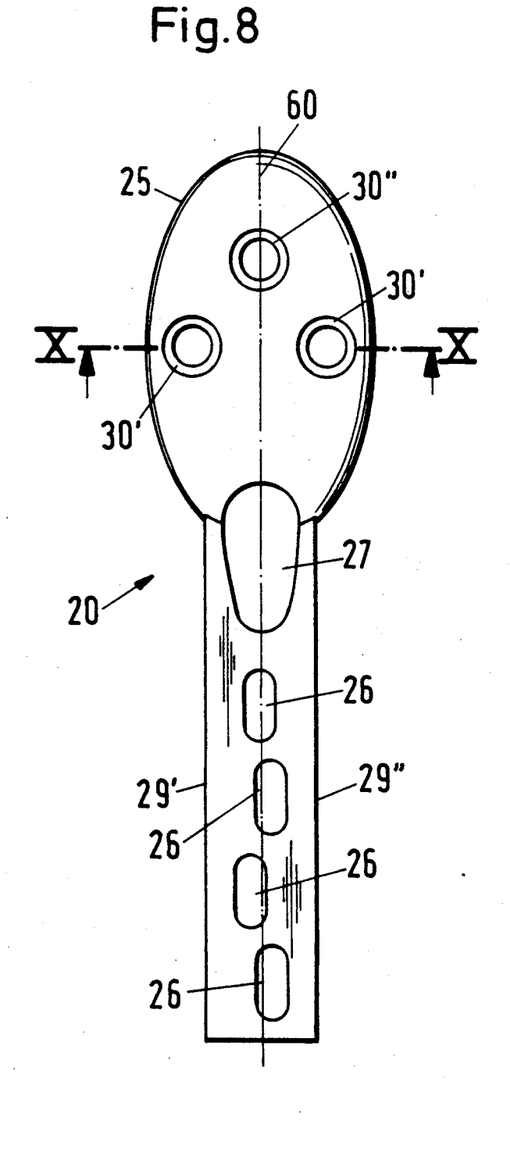
FIG. 8 shows a further embodiment of the trochanter supporting plate in a top view.
Figure 9:
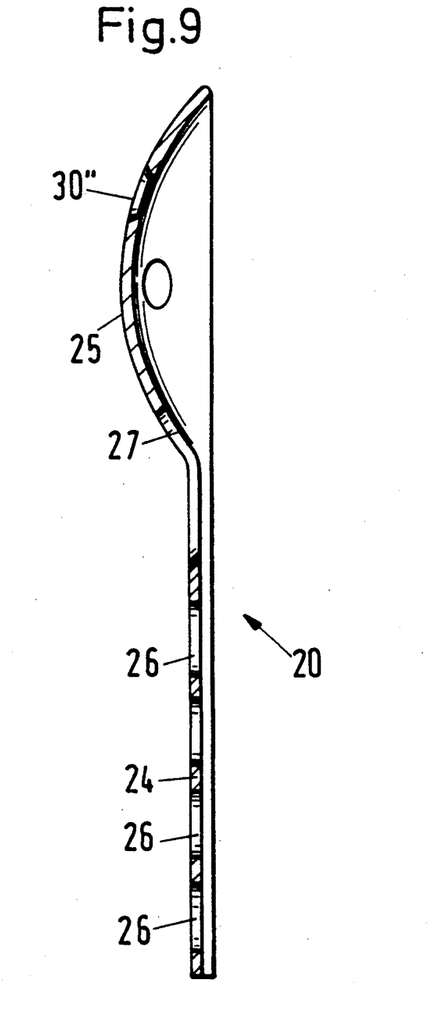
FIG. 9 shows the trochanter supporting plate according to FIG. 8 in a vertical longitudinal section.
Figure 10:
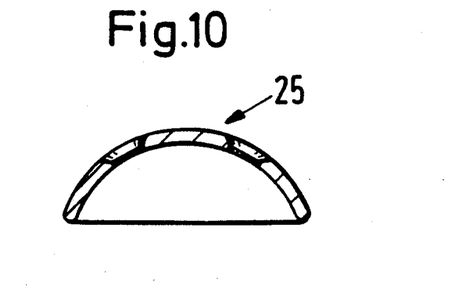
FIG. 10 shows a horizontal section along Line X—X in FIG. 9.
Figure 11:
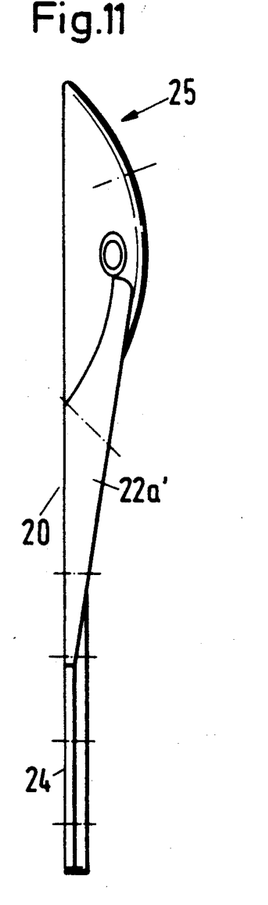
FIG. 11 shows the trochanter supporting plate in a side view.

In this embodiment, too, the trochanter supporting plate 20 is, within the transitional area of the cover plate-like section 29 to the plate-shaped section 25, provided with an ovaloid perforation 27 which serves for the passing through of the sleeve 15 formed onto the bone fastening cover plate 11 (FIGS. 12, 1 and 16). The perforations 26 in the cover plate-like web 29 are arranged staggered relative to each other, an arrangement of the perforations 26 as depicted in FIG. 8 being particularly advantageous, according to which the perforation 26 facing the plate-shaped section 25 is located on the concentric longitudinal axis 60, while the other perforations 26 are disposed alternately to the longitudinal axis 60 (FIG. 8).

Figure 14:
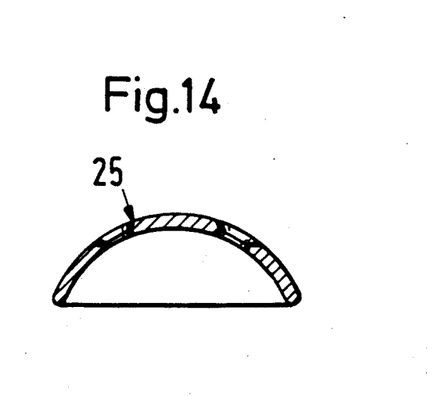
FIG. 14 shows a horizontal section along Line XIV—XIV in FIG. 12.

In the embodiment of a trochanter supporting plate 20 shown in FIGS. 12 to 14, the legs 22,23 on the cover plate-like section 29 or on its web 24, which, in the trochanter supporting plate 20 according to FIGS. 1 and 2, extend across the entire length of the web 24 up to the area of the plate-shaped and spoon-like constructed section 25, are constructed by sections and merely extend over the connecting area of the cover plate-like section 29 up into the section 25 as far as underneath the two lower perforations 30 in the section 25, so that solely the transitional area is reinforced and stabilized and, moreover, an adequate guiding of the bone fastening cover plate 11 exists.

Figure 17:
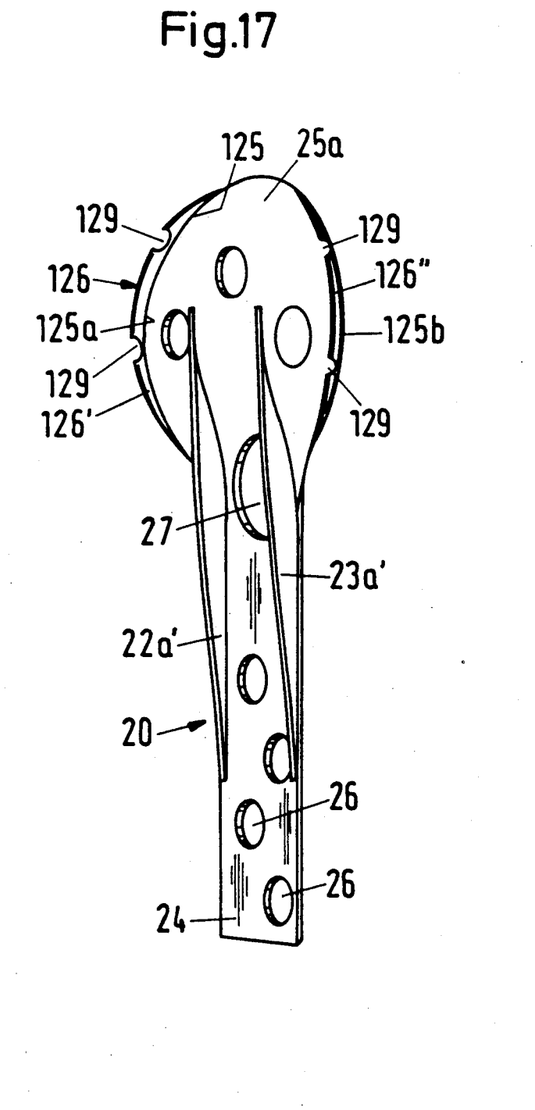
FIG. 17 shows, in a diagrammatical rear view, a trochanter supporting plate with means for fitting cerclage wires.
Figure 18:
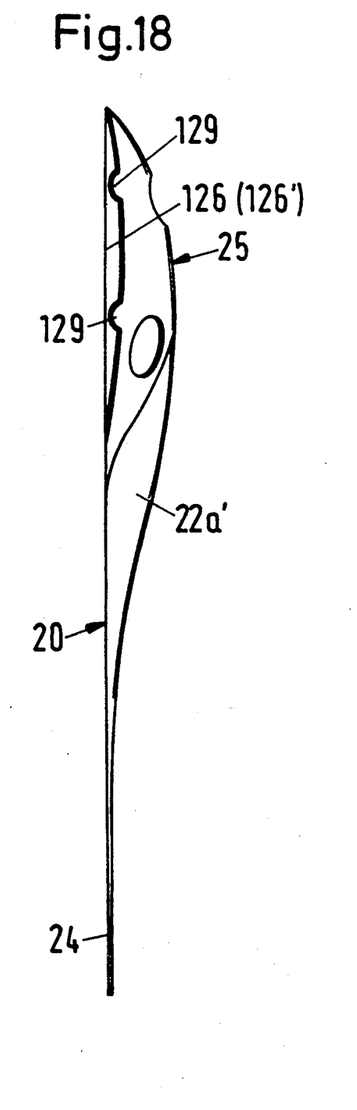
FIG. 18 shows the trochanter supporting plate according to FIG. 17 in a side view.

In those cases where, within the area of the greater trochanter, such a comminution exists that the osseous substance no longer lends itself to having screws inserted, a tying on and fixation with the aid of cerclage wires is necessary. For this purpose, the trochanter supporting plate 20 is provided with a connecting device 70 which renders a fixation of a cerclage wire or of several cerclage wires on the trochanter supporting plate 20 possible. Said connecting device 70 consists of a bending or folding over of the circumferential edge 125 of the plate-shaped and spoon-like constructed section 25 of the trochanter supporting plate 20 within the rearward area of the latter. This bent-over circumferential section 126 is constructed essentially within the central lateral areas 125a,125b of the circumferential edge 125 of the section 25 and thus extends to both sides of the section 25 of the trochanter supporting plate 20, so that two individual sections 126',126" are formed. The ends of the two individual areas 126',126" taper conically on both sides (FIG. 17).

In order to fix a cerclage wire not shown in the drawing, the bent-over section 126 or its individual sections 126',126" are provided with a number of slot-shaped cutouts 129.

What is claimed is:

1. Device for connecting a fractured bone, such as the femoral neck area, comprising a bone fastening cover plate with fastening perforations, said cover plate having a longitudinal direction extending parallel to the longitudinal axis of a bone to which it is to be connected by fastening means a sleeve carried by and positioned at an angle relative to the bone fastening member and a trochanter supporting plate, wherein the trochanter supporting plate (20) is detachably connectable to the bone fastening cover plate (11) and comprises an elongated plate-shaped section (29) corresponding approximately to and elongated in the longitudinal direction of the bone fastening cover plate (11), said plate shaped section has a web (24), one end (24a) of said web passes into a plate-shaped section (25) extending in the elongated direction and forming a trochanter supporting surface, the web (24) has two sides extending in the elongated direction with a reinforcing leg (22, 23) extending along each side for at least a partial length of the elongated web (24) and into a portion of the section (25), toward a terminal area (25a) of the section spaced from the web, and in the direction toward the terminal area (25a), runs out tapering conically, the bone fastening cover plate (11) of the device (10) is positionable between the two legs (22, 23) and is arranged to rest against the web (24) so that the section (25) forming the trochanter supporting surface projects in the elongated direction from the bone fastening cover plate (11) and an ovaloid perforation (27) for the passing through of the bone fastening member reception sleeve (13).

2. Device according to claim 1, wherein the plate-shaped section of the trochanter supporting plate (20) comprises a sectional member (21) having a U-shaped cross-section approximately corresponding in length to the bone fastening cover plate (11), the trochanter supporting surface has a spoon-like constructed section (25), with a concave surface and a convex surface, the two legs (22, 23) are located on the convex side of same spoon-like construction section and extend into the terminal area (25a) of the plate-shaped section (25).

3. Device according to claim 2, wherein the web (24) of the sectional member (21) of the trochanter supporting plate (20) has an outward bulge (28) of circular shape extending in the direction of the sectional member legs (22, 23).

4. Device according to claim 2 wherein the spoon-like constructed section (25) of the trochanter supporting plate (20) has a circumferential edge (125) bent over and extending away from the concave surface and forms a bent-over edge section (126) provided with a number of cerclage wire fixation cutouts (129), and the bent-over edge section (126), within the terminal area (25a) of the section (25) of the trochanter supporting plate (20) and within transitional areas of the webs (22,23,22',23a') between the cover plate and the trochanter supporting plate is constructed so as to extend conically tapering in the section (25).

5. Device according to claim 4 wherein the circumferential edge (125) of the spoon-like constructed section (25) of the trochanter supporting plate (20) forms two bent-over edge sections (126',126") on opposite sides of said spoon-like constructed section, and each edge section (126',126") has two terminal areas tapering conically.

6. Device according to any of the claims 4 or 5, wherein the bent-over edge sections (126',126") are provided with two cerclage wire fixation cutouts (129).

7. Device according to claim 1, wherein the ovaloid perforation (27) in the web (24) of the sectional member (21) of the trochanter supporting plate (20) is adapted to the different angular variables of the device (10).

8. Device according to claim 1, wherein the sectional member (21) of the trochanter supporting plate (20) is extensible by mountable sectional member parts.

* * * * *